United States Patent
Shoseyov et al.

(10) Patent No.: US 10,695,462 B2
(45) Date of Patent: Jun. 30, 2020

(54) ON-DEMAND DEGRADABLE MEDICAL DEVICES

(71) Applicants: Yissum Research Development Company of the Hebrew University of Jerusalem Ltd., Jerusalem (IL); Rambam Med-Tech Ltd., Haifa (IL)

(72) Inventors: Oded Shoseyov, Carmei Yosef (IL); Danny Porath, Jerusalem (IL); Ofra Benny, Mevasseret Zion (IL); Yaron Bar-Lavie, Zichron Yaakov (IL); Amos Ofer, Haifa (IL)

(73) Assignee: Yissum Research Development Company of the Hebrew University of Jerusalem Ltd. (IL)

( * ) Notice: Subject to any disclaimer, the term of this patent is extended or adjusted under 35 U.S.C. 154(b) by 156 days.

(21) Appl. No.: 15/516,805

(22) PCT Filed: Oct. 7, 2015

(86) PCT No.: PCT/IL2015/051001
§ 371 (c)(1),
(2) Date: Apr. 4, 2017

(87) PCT Pub. No.: WO2016/056008
PCT Pub. Date: Apr. 14, 2016

(65) Prior Publication Data
US 2017/0312388 A1 Nov. 2, 2017

Related U.S. Application Data

(60) Provisional application No. 62/060,678, filed on Oct. 7, 2014.

(51) Int. Cl.
*A61L 27/34* (2006.01)
*A61L 31/10* (2006.01)
*A61F 2/02* (2006.01)
*A61L 29/08* (2006.01)

(52) U.S. Cl.
CPC ............ *A61L 27/34* (2013.01); *A61F 2/02* (2013.01); *A61L 29/085* (2013.01); *A61L 31/10* (2013.01)

(58) Field of Classification Search
None
See application file for complete search history.

(56) References Cited

U.S. PATENT DOCUMENTS 5,176,907 A * 1/1993 Leong .................. A61K 9/0024
424/423
5,464,650 A * 11/1995 Berg ........................ A61F 2/82
427/2.25

(Continued)

OTHER PUBLICATIONS

PCT International Search Report dated Jan. 29, 2016 for PCT Patent Application No. PCT/IL2015/051001.
(Continued)

*Primary Examiner* — Peter A Salamon
(74) *Attorney, Agent, or Firm* — McAndrews, Held & Malloy, Ltd.

(57) ABSTRACT

The invention disclosed herein generally provides implantable medical devices and implants that may be removed on-demand from a subject's body at any time after their implanting in the body, without necessitating invasive procedures.

20 Claims, 5 Drawing Sheets

(56) References Cited

U.S. PATENT DOCUMENTS

| | | | | | |
|---|---|---|---|---|---|
| 5,906,639 | A | * | 5/1999 | Rudnick | B21F 45/008 623/1.15 |
| 5,999,482 | A | * | 12/1999 | Kornachuk | G11C 5/063 365/194 |
| 6,056,187 | A | * | 5/2000 | Acciai | A61F 2/90 156/304.2 |
| 6,071,308 | A | * | 6/2000 | Ballou | A61F 2/90 606/198 |
| 6,161,399 | A | * | 12/2000 | Jayaraman | D04B 1/14 623/1.5 |
| 6,306,166 | B1 | * | 10/2001 | Barry | A61L 27/34 623/1.42 |
| 6,333,347 | B1 | * | 12/2001 | Hunter | A61K 31/337 514/449 |
| 6,375,660 | B1 | * | 4/2002 | Fischell | A61F 2/95 606/108 |
| 6,428,811 | B1 | * | 8/2002 | West | A61K 41/0028 424/497 |
| 6,579,308 | B1 | * | 6/2003 | Jansen | A61F 2/88 623/1.15 |
| 6,815,609 | B1 | * | 11/2004 | Wang | A61N 1/16 174/391 |
| 8,128,689 | B2 | * | 3/2012 | Weber | A61L 31/022 623/1.42 |
| 8,216,632 | B2 | * | 7/2012 | Schoenle | A61L 31/082 427/2.25 |
| 8,353,949 | B2 | * | 1/2013 | Weber | A61F 2/82 427/2.25 |
| 8,449,603 | B2 | * | 5/2013 | Weber | A61L 31/088 427/2.1 |
| 2004/0030379 | A1 | * | 2/2004 | Hamm | A61K 31/335 623/1.15 |
| 2004/0254419 | A1 | * | 12/2004 | Wang | A61K 45/06 600/8 |
| 2005/0079200 | A1 | * | 4/2005 | Rathenow | A61L 27/303 424/423 |
| 2005/0107870 | A1 | * | 5/2005 | Wang | A61K 31/10 623/1.44 |
| 2007/0231363 | A1 | * | 10/2007 | Chen | A61K 9/0024 424/423 |
| 2008/0071353 | A1 | * | 3/2008 | Weber | A61L 31/148 623/1.15 |
| 2010/0003326 | A1 | * | 1/2010 | Vertommen | A61K 9/0009 424/486 |
| 2010/0317588 | A1 | * | 12/2010 | Shoseyov | C07K 14/43518 514/16.8 |
| 2014/0214175 | A1 | * | 7/2014 | Barron | A61F 2/04 623/23.66 |
| 2017/0312388 | A1 | * | 11/2017 | Shoseyov | A61L 27/34 |

OTHER PUBLICATIONS

Communication from the European Patent Office regarding European Patent Application No. 15 797 465.0, dated Jul. 11, 2019, 7 pgs.

* cited by examiner

ON-DEMAND DEGRADABLE MEDICAL DEVICES

CROSS-REFERENCE TO RELATED APPLICATIONS

This application is a National Phase Entry of PCT International Application No. PCT/IL2015/051001, which was filed on Oct. 7, 2015, and claims the benefit under 35 U.S.C. § 119(e) of U.S. provisional patent application Ser. No. 62/060,678, filed Oct. 7, 2014. The contents of each of the foregoing applications are hereby incorporated by reference.

TECHNOLOGICAL FIELD

The invention generally concerns on-demand degradable medical devices or implants and uses thereof.

BACKGROUND ART

A brief history of inferior vena cava filters and analysis of current devices Which Medical Device. 22 Mar. 2012. Ed. Dr Michael D Burns. *Expert Independent Opinion, Which Medical Device™*.

BACKGROUND

Implanted devices are extensively used in Medicine. Some are permanent and others have to be surgically or endovascularly extracted. Often the device is only needed for a short period, and in the long run may interfere with normal endothelial functions. Ideally a device would dissolve completely after a few weeks or months.

In a specific case, where such a central problem exists is the use of filters for minimizing or arresting mobilization of blood clots in the body. Blood clots may form due to disease or trauma. Their mobility may lead to severe and potentially irreversible deterioration of health, as pulmonary embolism or stroke may lead to death. In cases of a high risk of clot formation, filters are inserted in critical positions in the veins in order to prevent the risk of mobilization of clots to the lungs or to the brain. Currently these filters are made of permanent materials like metal. If these filters remain in the veins beyond the period necessary for prevention of clot mobilization, they may eventually entail damages by themselves. Most filters can be removed during a radiological procedure. However, since they usually do not cause pain or discomfort most patients do not return to the hospital for their removal. At times the filter may fuse with the vein and cannot be removed at all. The use of such filters in the USA is growing rapidly, from ~2000 in 1979 to ~260,000 in 2012. It was found that in about 80% of the patients the filters are unfortunately not removed.

Similar difficulties and risks are seen in the use of many temporary and permanent implants, such as stents, support systems, and many other implantable medical devices.

SUMMARY OF THE INVENTION

The inventors of the technology disclosed herein have endeavored to provide a solution to risks associated with permanent implantable devices and propose herein a novel approach and class of implantable medical devices or implants which may be induced to degrade on-demand, utilizing non-invasive procedures, or which are configured or engineered to autonomously degrade after a certain period of time. A non-invasive procedure would enable immediate (or within a short time period) degradation of the device, in cases where the device is no longer needed or, for example, when the device malfunctions or poses a danger to the subject at any time after implantation.

The non-invasive procedure may further enable manipulation of an implanted device to achieve a so-called "mechanical switch", for example, for the purpose of releasing pressure on a surrounding tissue, detaching/releasing part of the device, disconnecting two or more parts of the device from each other or effecting any other mechanical or structural change.

Thus, it is a purpose of the present disclosure to provide a novel implantable medical device or implant that may be permanent for a predefined period of time, or until such a time where the device operation or function is no longer necessary, or until such a time where the device poses a health risk to the subject, and thereafter may be degraded "on-demand", e.g., by application of a non-invasive external stimulus, e.g., application of an external energy source, such as Radio Frequency (RF).

As used herein, the terms "medical device" and "implant" are used interchangeably despite certain differences known in their utility and operation. Within the context of the present invention, both refer to a device or a feature which is suited for placing or implanting in a subject's body, e.g., body cavity or tissue, for a particular period of time. The device or implant induces an effect or functions or operates when in the body, with its size, shape, form, constitution and other physical, chemical and mechanical features being dependent on its intended use and may be completely customizable to the patient's personal needs.

Thus, in a first aspect of the invention, there is provided an implantable medical device (or an implant) comprising:
  a core of at least one biocompatible water-soluble material,
  a skin encasing (or coating or enveloping or sealing or isolating) the core, thereby protecting the core material from water-derived decomposition (or degradation or digestion);
  the skin (or envelope or film) being in the form of a continuous uninterrupted coat around the core, and selected from thermo-degradable (thermo-sensitive) biocompatible materials, being hydrolytically and physiologically non-degradable; and wherein the skin optionally comprising at least one radiation responsive element (e.g., which increases its temperature upon external radiation).

By another aspect, the invention provides an implantable medical device, the device comprising a core of at least one biocompatible water-soluble material, said core being hermetically encased or coated by a skin or an envelope which isolates the material of the core from the environment; the skin or envelope being in the form of a continuous uninterrupted coat around the core, the skin or envelope being or comprising a thermo-sensitive biocompatible material, wherein the skin or envelop material being hydrolytically and physiologically non-degradable.

In another aspect, there is provided an implantable medical device, wherein at least a part of the device comprising a core composed of a biocompatible water soluble material, said core having a desired physical property, the core being hermetically sealed by an envelope which isolates the core from the environment; the envelope comprising a thermo-sensitive biocompatible material that is intact, for a defined period of time, under physiological conditions present at the site of intended implantation, said envelope loses integrity upon rise in temperature to a non-physiological temperature that is tolerable by a living tissue.

The medical device or implant of the invention is a device suitable for implantation within a body cavity or in a subject's (human or non-human) tissue. The device is typically placed in the subject's body for medicinal purposes. In other words, the device may be in the form of an instrument, prosthetic, implement, contrivance, implant, in-vitro reagent, component, element, accessory or a part which is intended for therapeutic or diagnostic use, in the treatment or prevention or diagnosis of a disease or a condition in a human or an animal. In other cases the medical device is intended to affect a structure or a function of a body organ or tissue or to replace a missing body part.

The medical devices of the invention may be implanted as acceptable in the relevant field. For example, stents may be implanted differently from hip implants. Yet, unlike with traditional implants which removal from the body requires a second round of invasive measures, the extraction or otherwise elimination of the implants of the invention from the body may be achieved without invasive methods. For example, a fixation device of soft tissue such as hernia mesh or a fixation device of hard tissue in which part of the fixation device is a "Velcro-like" structure may be released/loosen on-demand, without necessitating invasive manipulations.

As will be further elaborated on below, the device of the invention is suited for implantation and residence in a body cavity or tissue for any period of time, which may or may not be pre-defined or pre-set, and under the physiological conditions of the cavity or tissue in the subject's body. In the absence of the skin or a material enveloping the core material, the core material, being water-soluble or water-degradable, decomposes or degrades or is digested and the medical device therefore loses its purpose and mechanical, physiological or otherwise distinctive characteristics. In order to protect the core material from decomposition and allow for a short- or medium or long-residence time in the body, the integrity of the skin must be maintained for the residence period of time. Thus, the core material is presented with a film or skin or envelope of a water-stable material which does not decompose or disintegrate under the conditions of the body cavity or tissue, e.g., at least for the period of time required by the specific medical indication. In other words, the skin does not undergo any chemical or mechanical decomposition or erosion which may affect its integrity and potentiate water penetration therethrough and subsequent decomposition of the core material. The film or skin or envelope of a water-stable material maintains its integrity within the body for any period of time.

The skin material is further selected such that it is not absorbable or is non-absorbable by the body tissues. While a skin material may be selected to have a minimal reaction to water such that its decomposition in a water-containing environment is slow, vis-à-vis the residence time of the device in the body, the skin material is selected to be stable in aqueous environments for at least the required period of time. The skin material loses its integrity during that stable period only upon rise in the skin temperature to a non-physiological temperature. Typically, such loss of integrity would occur only following application of an external energy source which is directed at the device and which directly or indirectly causes an increase in the temperature of the device skin to a temperature which causes its chemical or mechanical decomposition or under which temperature the skin integrity is reduced and the core material becomes exposed to the aqueous environment in which the device resides. The rate of increase in the temperature, and the maximum temperature are typically selected to be tolerable by the subject and non-damaging to the surrounding tissues.

The body cavity or tissue may be any space in the body of the subject or any tissue thereof, including for example the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and others.

In some cases the cavity is a natural cavity such as the lumen or channel within a tubular organ, such as a blood vessel or the intestine. In other cases the cavity is a surgically formed cavity, e.g., between an epidermis layer and an underlining tissue, or between soft and hard tissue.

The environment in which the device of the invention may be positioned is one which naturally contains water or water-containing fluids or tissues, such as soft and hard tissues, blood, urine, saliva, sputum, tears, semen, milk, cerebro-spinal fluid or vaginal secretions. The skin of the medical device is selected from materials resistant to decomposition when in contact with any one of these fluids, for at least a desired time period (for at least the residence time of the device in the body).

The medical device or implant of the invention may be fabricated to adopt any size and/or shape. In some embodiments, a device according to the invention is achieved by construction of a core, having a set of desired physical properties, including inter alia, shape, size, and strength. The core is subsequently sealed or coated or treated to form on its exterior surface (most exposed surface) a skin of a different material. The skin may be of any thickness, provided that it is continuous, intact, does not contain any pores, or at least does not permit permeation/penetration of water or water containing media therethrough; namely provided that the core is hermetically sealed and prevented from contacting its environment.

Typically, the skin coats the full three dimensional surface of the device core. In some cases, the device is constructed of different regions, where only one or more of said regions are to be degraded on-demand. In such cases, only regions of the device to be degraded or decomposed may be covered by a skin as disclosed. In some cases, the device is made by a textile technology such as weaving, knitting, braiding etc. The fiber is in the form of a core-shell structure, whereas the core is a water-soluble material and the shell is the sealing skin.

The core is the innermost part of a device of the invention and may be of any shape. In some embodiments, the core is of a three-dimensional structure and the coating skin is provided with varying thicknesses in order to endow controlled decomposition of the skin material; namely decomposition as a rate dependent on the skin thickness. In some cases, the core is exposed faster in regions where the skin is thinnest and slower where the skin is thickest.

In some cases the core is exposed faster where the concentration of responsive elements is higher, independently of the skin thickness, as will be further disclosed hereinbelow.

In other embodiments, the core is of a three-dimensional structure and the coating skin is provided with varying thicknesses in order to modify the shape and/or size of the implantable device. For instance, the core of the device may be spherical; yet the shape of the device may be rectangular, an external shape endowed by the shape of the core-coating skin.

The core is selected of at least one biocompatible water-soluble material or a composition of several water-soluble materials. As used herein, any material coming into contact with a body cavity or tissue must be biocompatible, namely of a material that is not toxic, injurious, physiologically reactive to the surrounding tissue and preferably also which does not cause immunological rejection. As noted, the core material is typically separated or isolated from the surrounding tissues by a skin. Thus, biocompatibility may come into play only once the core material has been exposed to the tissue and degradation or dissolution thereof commences.

The core material is also said to be of a water-soluble material. As used herein, "water solubility" refers to the ability of the core material to dissolve in the aqueous environment surrounding the device and eventually be cleared away from the site of implantation and the subject's body. In some embodiments, the biocompatible water-soluble material is selected from natural or synthetic amorphous or crystalline materials or combinations thereof.

In some embodiments, the water-soluble material from which the core is made may be selected from natural and synthetic carbohydrates, salts, organic polymers and derivatives thereof.

In some embodiments, the water-soluble material is selected from mono-saccharides, di-saccharides, oligosaccharides, polysaccharides and combinations thereof, active compounds such as water-soluble vitamins, amino acids, drug agents (pharmaceuticals), proteins, nucleotides, oligonucleotides, DNA, RNA and other materials.

In further embodiments, the water-soluble material is selected from glucose, fructose, dextrose, sucrose, manitol, sorbitol, starch derivatives, cellulose derivatives, guar gum, pectins, chitosan, agar, alginate, carrageenans, laminarin sugar alcohols and polyolefins. In some embodiments, the polyolefin is selected from polyvinyl alcohol, fully hydrolyzed polyvinyl alcohol, partially hydrolyzed polyvinyl alcohol, polyethylene glycol and polyethylene oxide.

In further embodiments, the water-soluble material is selected from polyacrylamides, polyacrylic acid, polyisocyanates, cationic polyelectrolytes or salts, such as NaCl.

In further embodiments, the water-soluble material is selected from xylitol, polyethylene oxide and "carbohydrate glass" (a mixture of glucose, sucrose, dextran and water, being in the form of a liquid glass (see for example: Miller et al. 2012, Rapid casting of patterned vascular networks for perfusable engineered three-dimensional tissues. Nature Materials, 768-774).

In some embodiments, the core is made of natural or synthetic or semi-synthetic fibers. In some embodiments, each fiber may be separately provided with a skin of at least one thermo-sensitive material. In further embodiments, the fibers so provided are formed into a woven, net-shape, mesh-shape, filter or otherwise a device or an element of a device. In some embodiments, the device is an Inferior Vena Cava (IVC) filter or a vascular stent or a coil or a graft or a mesh or a tube or a sheath.

Figure 1:
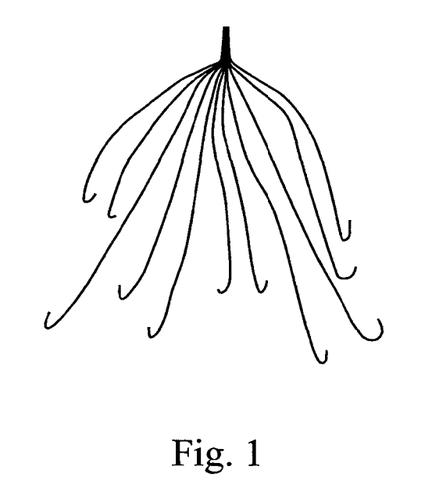
FIG. 1 is a structural depiction of an IVC device according to certain embodiments of the invention.
Figure 2A:
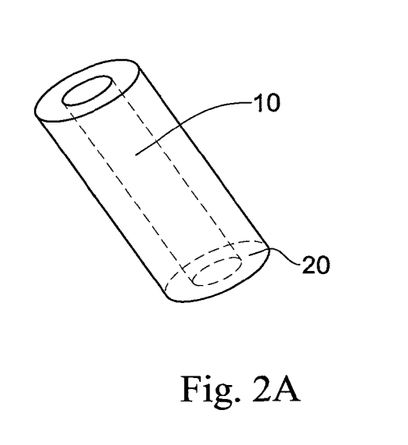
FIGS. 2A and 2B are side view (FIG. 2A) and cross-sectional view (FIG. 2B) of a leg of a device depicted in FIG. 1.
Figure 2B:
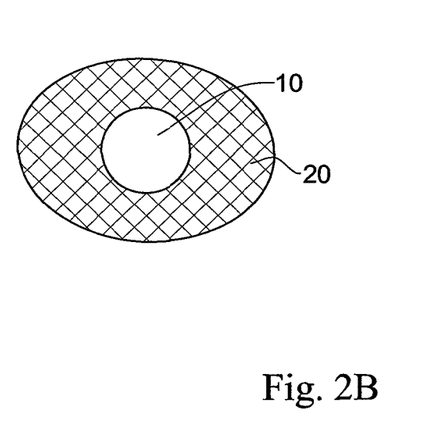
Figure 3:
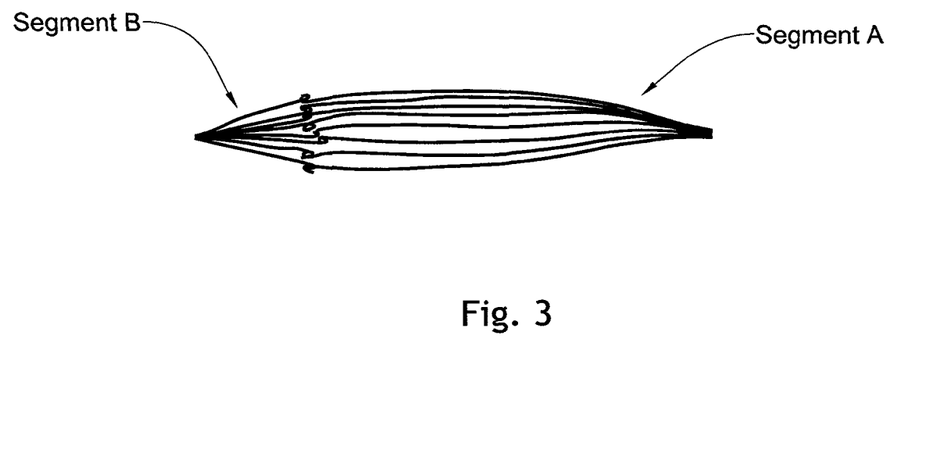
FIG. 3 is a structural depiction of a device according to certain embodiments of the invention.

An exemplary device according to the invention is provided in FIGS. 1 through 3. In FIG. 1 a traditional IVC filter is depicted in an open form, with the device numerous legs extending to form the device tulip-shape. Each of the device legs are constructed in a core-shell form, as depicted in FIG. 2A (side-view) and FIG. 2B (cross-section view of a device leg), wherein a core region 10 comprises a water-soluble material and a skin 20 region comprising a thermo-sensitive material hermetically sealing and protecting the core from water-derived degradation.

The skin isolating the core material from the surrounding is selected from at least one thermo-degradable (thermo-sensitive) and thermoplastic biocompatible material. These materials are selected to be hydrolytically non-degradable (do not degrade upon contact with water) and physiologically non-degradable (do not degrade upon contact with physiological environment containing biological agents and conditions) and optionally comprising at least one radiation responsive element (e.g., which increases its temperature upon external radiation).

The at least one thermo-degradable or thermo-sensitive material is a material that is stable under the physiological conditions of the subject's body, vis-a-vis inter alia, water content, acidity, presence of salts, enzymes and other biological agents, and temperature; and which undergoes decomposition, degradation and subsequently excretion only upon an increase in its temperature (brought about by external radiation). In other words, the thermo-sensitive material is selected to be in a solid form at a body temperature, and in a different form at a higher temperature. The different form may be liquid, gel, granulated form, form of drops, solute, and any other form which permits eventual clearance from the implantation site.

In some embodiments, the thermo-sensitive material maintains a solid form at a temperature below 80° C. (degrees centigrade). In some embodiments, the thermo-sensitive material maintains a solid form at a temperature below 70° C., 60° C. or 50° C. In some embodiments, the thermo-sensitive material is in a solid form at a temperature below 40° C. In some embodiments, the material maintains a solid form at a temperature between 35 and 40° C.

In some embodiments, the thermo-sensitive material undergoes a form change above 80° C. In some embodiments, the thermo-sensitive material undergoes a form change above 70° C., 60° C. or 50° C. In some embodiments, the thermo-sensitive material undergoes a form change above 40° C.

In some embodiments, the thermo-sensitive material is selected to have a glass transition temperature (Tg) at or around 80° C. In some embodiments, the Tg is at or around 70° C., 60° C. or 50° C. In some embodiments, the Tg is above 40° C.

The temperature under which the thermo-sensitive material is degraded is a temperature which is tolerable by the surrounding tissues or organs and which does not cause any discomfort or health risk to the subject.

The thermo-sensitive material may be of any constitution or composition provided that it is water-insoluble and does not decompose under the physiological conditions of the subject, as further discussed herein. In some embodiments, the thermo-sensitive material is a biocompatible polymer. In some embodiments, the thermo-sensitive material is selected amongst thermoplastic polymers.

In some embodiments, the biocompatible thermo-sensitive water-insoluble polymers include poly(acrylamide)s, poly(acrylic acid)s, poly(adipic anhydride)s, poly(7-aminoenanthic acid), poly(12-aminolauric acid), poly(azelaic anhydride), poly(1,3-butadiene-1,4-alt-methacrylonitrile), poly(1,3-butadiene-1,4-alt-methylmeth acrylate), poly(butadiene oxide)s, poly(caprolactone), poly(caprylaldehyde), poly(1,4-cyclohexylenedimethylene azelate)s, poly(1,4-cyclohexylenedimethylenedodecane dioate), poly(1,4-cyclohexylenedimethylene glutarate), poly(1,4-cyclohexylene dimethylene)-oxymethylene oxide, poly(1,4-cyclohexylenedimethylene p-phenylene diacetate), poly(1,4-cyclohexylenedimethylene pimelate), poly(1,4-cyclohexylene dimethylene sebacate), poly(1,4-cyclohexylenedimethylene suberate), poly(cyclo hexylidenethiohexamethylene sulfide), poly(cyclopropylenedimethylene isophthalate), poly (cyclopropylenedimethylene piperazinediurethane), poly (cyclopropylidene dimethylene oxide), poly (decamethylene), poly(decamethylene carbonate), poly (deca methylene 3,3'-dibenzoate), poly [(decamethylenedioxy)-dihexamethylene oxide], poly (decamethylene disiloxanylenedipropionamide), poly(decamethylene disulfide), poly (decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene 3,3'-methylenedibenzamide), poly[decamethylene (methylene-2,5-tetrahydrofuran)-dicarboxamide], poly(deca methylene oxydiacetate), poly(decamethyleneoxymethylene oxide), poly(deca methylene sulfide), poly(decamethylene thiodivalerate), poly(decamethylene thiohexamethylene sulfide), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosa methylene sebacate), poly(eicosamethylene suberate), poly(eicosamethylene succinate), poly(eicosamethylene thiodivalerate), poly[ethylene p-(carboxyphenoxy)-caproate], poly[ethylene p-(carboxyphenoxy)-heptanoate] and poly[ethylene p-(carboxyphenoxy)-undecanoate].

The skin may consist or comprise of at least one thermo-sensitive/thermoplastic material, as defined. In order to control, modulate, enable or assist in the eventual on-demand degradation of the skin material, the skin material may comprise in addition to the at least one thermo-sensitive material a selection of additional materials. Such materials are selected based on a variety of factors, inter alia, the type of implant, the three-dimensional shape and size of the implant, the residency period inside the body, the nature of the implant (namely its intended use and corresponding features), the process by which the skin is formed around the core material, the nature and constitution of the core material, and others.

In some embodiments, the materials are selected to set a pre-defined temperature difference between the core and skin materials. For example, where the implant is in the form of a core-shell fiber produced by co-extrusion, the core and shell materials are selected or engineered such that their respective melting temperatures are ideally close, e.g., exhibiting a melting temperature difference of no more than 20° C., or no more than 10° C.

In some embodiments, the skin comprises at least one thermo-sensitive material and at least one additive. The at least one additive may be selected from binders, film forming agents, solubilising agents or solubilization-arresting agents, disintegrants, lyophilizing agents, stabilizers, adhesive materials, surfactants, toxicity reducing agents, heat conducting agents, radiation responsive elements, magnetic materials (or particles), contrast agents, nanoparticles, gold-based materials and any material that upon external radiation, such as RF, ultrasound or any form of radiation, such as light, sound, electromagnetic or radioactive radiation will cause a temperature increase of the skin or any part thereof. The at least one additive may be utilized in any form, e.g., particulate or non-particulate forms.

In some embodiments, the at least one additive is a medicinally active material, e.g., a drug. The material may be any diagnostic, therapeutic, or prophylactic agent.

In some embodiments, the skin comprises further at least one surfactant.

In some embodiments, the skin further comprises at least one metal or composite inclusions that upon external irradiation heat up and emit heat to their surroundings, such may be selected to assist in or induce thermal conductivity or thermal dispersion and heat flow throughout the skin.

In some embodiments, the skin comprising at least one thermo-sensitive biocompatible material is embedded with at least one biocompatible material, e.g., in the form of particles, the material being capable of absorbing radiation and facilitating energy transfer throughout the skin material, thereby elevating the temperature of the skin material to a temperature higher than the body temperature (namely increase the temperature to the non-physiological temperature that is tolerable by the subject, and at which the skin material undergoes a form change, as detailed hereinabove).

The at least one radiation responsive element may thus be selected amongst particulate materials.

In some embodiments, the at least one radiation responsive element is selected amongst metal, metal-oxide, core-shell, core-multiple shell and hybrid nanoparticles.

In some embodiments, the at least one radiation responsive element (material) is selected from gold nanoparticles, iron oxide nanoparticles, gold/$SiO_2$, and other core-shell or hybrid nanoparticles of which temperature can be elevated under external radiation.

In some embodiments, the at least one radiation responsive material is selected amongst oxide nanoparticles, e.g., iron oxide nanoparticles. In some embodiments, the at least one radiation responsive material is selected amongst oxide magnetic nanoparticles (MNP).

In some embodiments, the at least one radiation responsive material is selected from gold nanoparticles (GNP).

In some embodiments, the at least one radiation responsive material is selected amongst oxide nanoparticles and gold nanoparticles and combinations thereof.

The at least one radiation responsive materials may be distributed within the skin of the implant of the invention prior to or subsequent to the formation of the skin around the core. In some embodiments, the at least one radiation responsive materials are distributed within the skin material prior to forming an envelope around the core, thereby controlling the concentration and final distribution of the materials in the skin.

For certain application, a homogenous distribution of the at least one radiation responsive material in the skin is necessary. In other cases, the materials may be distributed either at certain locations of the skin or at varying concentrations along the skin. In some embodiments, the materials may be distributed homogenously or in a form specifically pre-selected in order to achieve efficient degradation of the thermo-sensitive skin material and subsequent efficient elimination of the material from the body. For example, in some embodiments, the at least one radiation responsive material may be dispersed or rearranged within the thermo-sensitive skin to form a net or a mesh which upon heating causes decomposition of the thermo-sensitive materials into small material drops, the size of the drops being dependent on the distance or shape or volume or area between the net or mesh veins.

In some embodiments, the at least one radiation responsive material is distributed in the skin material at different depths in order to permit or make facile heat distribution into the depths of the skin material.

Once the core and skin materials are selected as provided herein, the implant of the invention may remain intact in the body for a period of at least few days, few weeks, few months or few years. As may be necessary, the implant of the invention may reside in the body for even longer periods of time and in some cases permanently.

An implant of the invention may be of any form, size and shape and may be constructed for a variety of therapeutic, diagnostic or cosmetic applications. In some embodiments, the entire implant is constructed of a core and skin materials and is configured for complete dissolution or removal from the body. In other embodiments, the implant is constructed of a non-degradable skeleton or element which may remain intact after the core and skin materials have been stripped off (decomposed or removed from the body).

In some embodiments, the implant comprises an underlying structure made from a metallic material or an alloy.

In some embodiments, an implant according to the invention is one which has at least one region thereof characterized by core and skin regions, as disclosed. In other words, some devices or implants of the invention may only partially be decomposable by irradiation.

In some embodiments, the implants of the invention may be selected from stents, e.g., coronary stents, vascular stents including peripheral stents and graft stents, urinary tract stents, urethral/prostatic stents, rectal stent, oesophageal stent, biliary stent and pancreatic stent, electrodes, catheters, leads, implantable pacemaker, cardioverter or defibrillator housings, joints, screws, rods, mesh, orthopedic implants, "Velcro-like" structures, ophthalmic implants, femoral pins, bone plates, grafts, anastomotic devices, perivascular wraps, sutures, staples, shunts for hydrocephalus, dialysis grafts, colostomy bag attachment devices, ear drainage tubes, bone pins, suture anchors, hemostatic barriers, clamps, screws, plates, clips, vascular implants, tissue adhesives and sealants, tissue scaffolds, intraluminal devices, vascular supports, balloon-expandable devices, coils, filters, grafts, meshes, sheaths and any other supporting device grafts.

The implant may be positioned in the subject's body during a surgical procedure or otherwise an invasive or minimally invasive medical procedure. In some cases, the implant insertion and deployment are carried out with full visualization of the procedure, during, e.g., enteral or urological procedures, or under radiological angiographic imaging procedures as is the case with vascular procedures.

Once removal of the implant is necessitated, the implant may be irradiated with an energy source in order to affect on-demand degradation of the thermo-sensitive skin material and eventual dissolution of the core material. The term "on-demand" refers herein to the choice presented to the medical practitioner to conclude that the implant may be, should be, or must be removed from the body via non-invasive methods; a decision that may be based on medical parameters that one or more of the following has occurred: (1) that the implant is no longer necessary, (2) that the implant no longer functions, (3) that the implant has lost its integrity, (4) that the implant is not appropriately positioned in the body, (5) that the implant has malfunctioned, (6) that the implant needs replacement, (7) that the implant poses a health risk to the subject, (8) in case of drug-loaded implants—that another drug dose is necessary, (9) in case of expandable implants—that the implant may be expanded into position, or others. Once such a conclusion has been reached, the temperature of the skin material may be increased by directing towards the implant or its environment thermal radiation. As used herein, "thermal radiation" refers to applying (for example by pulsing, etc) a thermal dose by means of radiation of a desired spectral signature or profile, namely frequency, as a function of intensity and exposure time.

As known in the art, the exact change in temperature is a function of field intensity and frequency, device environment and its thermal coupling to the environment, as well as the time of field application. Devices of the invention may be operable under a great variety of magnetic field intensities such as from 50-300 Gauss and frequencies of, for example, 100-550 kHz. Under such operation parameters a temperature increased by up to 35° C. in 5 seconds; or up to 50° C. in 10 seconds and up to 100° C. in 3 minutes may be achieved.

The heating process of a device according to the invention may be highly selective. As magnetic or metallic material absorb significant amounts of energy from applied electromagnetic fields, indirect heating of the device surroundings (e.g., by thermal coupling to hot metallic nanoparticles embedded in the skin of the device, as disclosed) may be achieved. The indirect heating may be kept low due to the low mass and heat capacity ($C_p$) of the heated materials, as well as the very fast changes in temperature, as demonstrated herein. For example, in aqueous environment local heating of a polymer by 31° C. in 8 seconds was measured while the temperature of the surrounding water increased by less than 1° C.

In some embodiments, thermal radiation may be in a form selected from IR, NIR, US, AC induced magnetic or electric field, radio frequency (RF), AC magnetic field and AC electric field.

Degradation of the thermo-sensitive skin material may be achieved by directing a source of external energy (e.g., IR, NIR, US, AC induced magnetic or electric field, radio frequency (RF), AC magnetic field and AC electric field) towards the implant. In some embodiments, the implant is heated to a temperature above 40° C. In other embodiments, the implant is heated to a temperature above 50° C. In other embodiments, the implant is heated to a temperature above 60° C. In other embodiments, the implant is heated to a temperature above 70° C. In other embodiments, the implant is heated to a temperature above 80° C. In other embodiments, the implant is heated to a temperature of between 40 and 80° C.

In some embodiments, magnetic field intensities of between 50-300 Gauss are used. In other embodiments, the device is irradiated at a frequency between 100-550 kHz.

In further embodiments, the magnetic field intensities are between 50-300 Gauss at frequencies between 100-550 kHz.

In some embodiments, the magnetic field intensity is 50, 75, 100, 150, 200, 250 or 300 Gauss. In other embodiments, the magnetic field intensity is between 100 and 300 Gauss. In other embodiments, the magnetic field intensity is 100, 110, 120, 130, 140, 150, 160, 170, 180, 190, 200, 210, 220, 230, 240, 250, 260, 270, 280, 290 or 300 Gauss.

In some embodiments, the frequency is 100, 150, 200, 250, 300, 350, 400, 450, 500 or 550 kHz. In some embodiments, the frequency is between 300 and 550 kHz.

In some embodiments, the frequency is 300, 350, 400, 450, 500 or 550 kHz.

In some embodiments, the magnetic field intensity is 100, 110, 120, 130, 140, 150, 160, 170, 180, 190, 200, 210, 220, 230, 240, 250, 260, 270, 280, 290 or 300 Gauss and the frequency is 100, 150, 200, 250, 300, 350, 400, 450, 500 or 550 kHz.

In some embodiments, the intensity is 150 gauss and the frequency is between 100 and 300 kHz, between 300 and 400 kHz, or between 400 and 550 kHz.

In some embodiments, the frequency is 266 kHz, 308 kHz, 382 kHz or 550 kHz.

In some embodiments, the implant is exposed to the energy source for a period of between several seconds to several minutes. In some embodiments, time of exposure is reduced with an increase in the temperature.

The thermo-sensitive skin of the implant may comprise or may be modified, engineered or fabricated to respond differently to different doses of energy, different frequencies or different exposure times. Such selective sensitivity may be achieved, inter alia, by fabricating the skin from different regions of different thermo-sensitive materials, different mixtures of thermo-sensitive materials, the presence or absence of (different or same) radiation responsive materials, concentration of the radiation responsive materials and others. For example, in some embodiments, to achieve selective degradation, the skin may be constructed of different material regions, each region comprised of a different thermo-sensitive material.

Such selective degradation allows construction of implants which final position or final form in the body may be manipulated externally by application of thermal radiation.

As used herein, the term "degradation" or "decomposition" or any lingual variation or art-recognized synonym thereof refers to degradation of a material into its component subunits, subsequent to, together with, or independent of a phase change (e.g., solid to liquid). Without wishing to be bound by theory, as degradation of a material depends on a multitude of factors, including chemical composition, nature of the bonds forming association between the material subunits, molecular weight, crystallinity, thermo- or biostability, absence or degree of cross-linking, site of implant, neighboring tissues and others, the degradation may proceed via different biological, chemical or mechanical pathways, e.g., a combination or any one or more of melting, hydrolysis, homogenous bulk degradation, surface erosion or mixed mechanisms.

In another aspect, the invention provides a medical device or implant, the device comprising:
  a structure;
  at least one biocompatible water-soluble material coating at least a region of said structure;
  a skin encasing (or coating or enveloping or sealing or isolating) the core material (protecting said core from water-derived decomposition), the skin comprising at least one first thermo-sensitive biocompatible material; and
  an element holding the expandable medical device in a compressed position; the element comprising at least one second thermo-sensitive biocompatible material;
  wherein the first and second thermo-sensitive biocompatible materials undergo decomposition under different thermal radiation parameters (thermal dose, frequency, temperature).

An exemplary IVC filter device is depicted in FIG. 3, wherein in an IVC filter, Segment A is forced into a form suitable for facile delivery into the body by Segment B. Segments A and B are each structured according to the invention. Each of the legs of the filter depicted in Segment A is a core-shell structure, wherein the core comprises a water-soluble material and a skin of a thermo-sensitive material. Segment B is similarly constructed, wherein the core material may or may not be the same as that in Segment A; yet the skin material of Segment B is different from the skin material of Segment A in at least one of their spectral parameters, as disclosed herein. This permits selective on-demand degradation of the skin material of Segment B, once the device has been positioned, and release of Segment A to expand into its normal tulip form (depicted in FIG. 1).

In some embodiments, the core material comprises at least one additive, e.g., drug, which upon core dissolution is released.

The selection of thermo-sensitive materials, each with a different sensitivity to thermal radiation, permits selective decomposition of one of them while keeping the other intact. For example, in expendable devices such as tissue support devices, e.g., stents, the element may be used to keep the stent in a folded or compressed form, or may generally in a form that endows the device with stiffness or form which manipulation in vivo may be further necessitated. On-demand, the stent may be irradiated by thermal radiation of a specific dose, frequency or temperature, which are different from those known for the thermo-sensitive material coating the core, thereby causing selective decomposition of the element and subsequent transformation of the device from a compressed form to an expended form, while keeping uninterrupted and intact the thermo-sensitive material coating the core. At a later stage, on-demand, the stent may be irradiated again with a thermal radiation suitable for degrading the skin of the core.

In some embodiments, the structure of the device, its skeleton, may be made from a metallic material or an alloy or from a shape memory material such as nitinol, stainless steel, other super-elastic metal alloys, or polymeric materials.

As with other devices of the invention, the thermo-sensitive materials may or may not comprise at least one radiation responsive material. In some embodiments, the thermo-sensitive material may comprise or consist of a material having a Tg of between about 40 and 60° C.

The invention further provides a delivery platform for on-demand release of a drug or a pharmaceutical or a diagnostic agent, the delivery platform being any of the devices of the invention, as disclosed herein, wherein the drug or pharmaceutical or diagnostic agent is comprised in the skin material and/or the core material and is released to the body once either the skin or the core are decomposed or dissolved as detailed herein.

In some embodiments, the drug is contained in the core, the skin or in a special drug layer separating the core material from the skin material. In some embodiments, the core and/or the skin are constructed of multiple layers, wherein at least one layer comprises a drug in a therapeutically acceptable form and amount.

Thus, the invention further provides long-term or short-term on-demand therapeutic methods for delivery of at least one drug material into a body region of a subject, wherein the method comprises implanting a device of the invention, the core and/or skin thereof comprising at least one drug.

The drug may be any pharmaceutically acceptable agent, a biomolecule, a small molecule, or cells. Non-limiting examples of such materials include, inter alia, anti-proliferative agents, biomolecules, antibodies, oligonucleotides, genes, carbohydrates, angiogenic factors, cell cycle inhibitors, hormones, nucleotides, amino acids, sugars, lipids, stem cells, progenitor cells, endothelial cells, adult cardiomyocytes, bone marrow cells and smooth muscle cells.

In some embodiments, the drug component is provided in nanoparticles, nanocapsules, microparticles, microcapsules, liposomes, micelles, vesicles, or any other known drug delivery vehicle.

In some embodiments, the medical devices and methods of the invention are suitable for treating or preventing a disease or disorder. The disease and disorder may be any such condition which may be treated or prevented by release of an active material at the site of implant.

Particular disease and disorders may include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and others.

The invention further provides an implantable device or an implant constructed of a plurality (two or more) of elements or segments, each of the elements or segments being associated to another of said elements or segments; wherein each element or segment is constructed of a core and a skin hermetically surrounding the care, as disclosed and defined herein, each skin being configured of at least one thermo-sensitive material, such that each material is sensitive to a different thermal radiation (frequency, dose, temperature). Such a device or implant may be positioned within a body of a subject and on-demand irradiated to cause sequential decomposition or degradation of a different element or segment of the device.

In some embodiments, the implant is configured of two or more such segments, each segment comprising a core material, as defined, further comprising at least one drug (the drug in each segment may or may not be the same); whereby sequential irradiation with thermal radiations suitable and selective to each segment, causes decomposition of said segments in sequence, at a rate and time desired, permitting delayed, slow, or sequential release of different drugs (in case each segment comprises a different drug) or drug dosages (in case each segment comprises the same drug, in the same or different amount).

By another aspect the present invention concerns methods for fabricating a device of the invention. Generally speaking, devices according to the invention, depending, inter alia, on their sizes, shapes, material composition and three-dimensional complexity may be fabricated by any of the methods known in the art.

In further embodiments, the implant on its components, including core and skin, may be fabricated by 3D printing, as known in the art. The core may be printed separately and then the skin may be formed by coating. Alternatively, the core-shell device maybe printed simultaneously.

In some embodiments, the core made of a water-soluble material may be molded, machined or 3D printed. In some embodiments, the skin of the thermo-sensitive material may be formed on the core by dipping or spraying.

In some embodiments, the device is fabricated of a plurality of fibers, each fiber comprising a core and skin (shell) and the fibers are woven or knitted or braded or otherwise intercalated with each other to form a final device.

In some embodiments, a woven device is fabricated by melting or wet extrusion of a water-soluble core, which is subsequently dipped in or sprayed with at least one thermo-sensitive material to form a coating of the thermo-sensitive material hermetically around the core, which are thereafter netted, braded or weaved into a desired 3D structure.

In an additional aspect, the invention contemplates a method for imaging a device in vivo, the method comprising imaging a device according to the invention for determining at least one of: (1) location of the device immediately following implantation in the body; (2) location of the device following a period of time after implantation in the body; (3) decomposition progress; (4) mechanical changes; (5) proper operation or malfunctioning of the device; (6) release of materials from the device; and (7) pre-decomposition decisions. The imaging may be achieved by any imaging method known in the art.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Implemented devices are extensively used in Medicine. Most are permanent, some have to be surgically or endovasculaly extracted, a few are degradable, but none are degradable upon demand Popular examples are Inferior Vena Cava (IVC) filters, vascular stents and coils, stent-grafts and urological catheters. Vascular stents, IVC filters and stent-grafts are usually made of stainless steel or metallic alloy.

Vascular stents are small mesh tubes that essentially prop open plaque-narrowed arteries. Most stents are used to treat coronary artery disease (CAD). The number of stents implanted in the USA differs according to various sources but most estimated to be 600,000 to 700,000 annually.

The vascular stent is needed to address the acute complications of the pathologic lesion: They improve immediate outcomes, by acutely opening vessel occlusions and scaffolding intimal tissue flaps that have separated from deeper layers, thus optimizing vessel caliber. They limit re-stenosis by preventing negative remodeling. The intimal hyperplastic healing response that contributes to re-stenosis can be limited by coating stents with anti proliferative medications.

Having a metal frame embedded in the arterial wall has long-term disadvantages: incomplete healing can induce a chronic inflammatory state, increasing the risk for thrombosis. Permanent stents can also impair endothelial function, prevent late favorable remodeling, and hamper future imaging and re-intervention. Loss of vasomobility is another disadvantage of stents. Arteries are meant to be dynamic: this allows them to enlarge to accommodate atherosclerosis or in response to increased demand, whereas a caged metallic structure confers rigidity on the artery.

An ideal stent should furnish best acute outcomes by sealing intimal flaps and optimizing lumen size. It should control re-stenosis by limiting negative remodeling and by controlling excessive healing by delivery of an anti proliferative drug. Beyond a few months, a permanent implant has no useful function and has possible disadvantages including the potential for late thrombosis.

Thus, the concept of a stent that does its job and then disappears has a great appeal. A number of different materials ranging from magnesium to a variety of polymers have been used to construct stents of different designs. Most bio-resorbable or degradable stents are made of polylactic acid, a naturally dissolvable material that is used in medical implants such as dissolving sutures. Drawbacks of using polymers include recoil after expansion, stent thickness causing maneuverability and crossing issues, difficulty visualizing a non-metallic stent on fluoroscopy and stents that do not sit firmly on delivery balloons. There are at least 15 degradable stent programs in progress, with five in advanced development stages and two having received European CE mark approval. The best outcomes to-date have been with the Abbott Vascular Bioresorbable Vascular Scaffold (BVS), where in the Absorb trial the stent was safe in a small number of patients with simple lesions. Indeed, there is a suggestion of luminal enlargement between 6 months and 2 years, return of vasomotion, and endothelial function.

Inferior Vena Cava (IVC) Filters

Between 100,000 and 300,000 Americans die annually from pulmonary embolism (PE)—more than breast cancer and HIV combined—representing the third leading cause of death. A similar incidence of PE is found in Europe with approximately 370,000 annual deaths. An estimated 25% of all hospitalized patients develop deep vein thrombosis (DVT). On average, 33% will progress to symptomatic PE of which 10% will be fatal. The usual treatment for DVT and PE is anticoagulation or thrombolysis with medications. However, many patients are unable to receive preventive or therapeutic anticoagulation because of co-morbidities or complications and thus are candidates for implantation of an IVC filter device.

The aim of the filter is to prevent the passage of blood clots from the lower extremities and pelvis to the lung, thus preventing the formation of a potentially lethal PE. Multi trauma patients, who are in danger of developing DVT and/or PE but cannot receive anti coagulation for danger of bleeding, are also candidates for an IVC filter. It has been estimated that 259,000 such filters were placed in 2012 in the USA alone. As with any other medical devices the presence of the filter in the IVC can cause complications such as thrombosis, occlusion of the IVC, perforation of the IVC's wall and migration of the whole filter or parts of it. Most of the filters used are temporary or retrievable: they can be extracted by an endovascular procedure which is carried out by an interventional radiologist.

In 2011 the FDA issued a safety alert stating that filters should be removed if possible. In spite of the above, for various reasons, up to 80% of the implanted filters are not removed. To address these issues attempts were made to develop filters that will degrade over time. Another solution is a convertible filter: a filter that loses its central parts over time and thus converts into a permanent stent.

The devices of the invention degrade, whether a coronary vascular stent, an IVC filter or any other implanted device, when needed. The need can arise immediately if the device is improperly deployed or has migrated, or when the device is no longer needed. Thus, each patient, with her/his specific device and specific medical situation, will have the ability to have their device degraded on-demand when no longer needed. This is personalized medicine at its best.

Another feature of current implantable vascular devices is that they come in a fixed factory made size, length and form. This may often lead to difficulty in adjusting the device to the patient's vascular anatomy. In contrast, the geometrical and three-dimensional properties of the new devices of the invention may be customized and adjustable to the patient's personal anatomy.

In accordance with specific embodiments of the invention, implants are degradable in situ, e.g., by RF, with following properties:

(1) low melting point (40-60° C.) to avoid tissue damage;
(2) Sufficient mechanical strength to resist physiological flow conditions;
(3) Elasticity and shape refinement capabilities;
(4) Rapid degradation upon external stimuli to avoid circulation of fragments in blood stream.

Two exemplary biocompatible polyester mixtures were used: Poly L-lactic Acid (PLLA) and Poly Caprolactone (PCL), at various combinations, as listed in Table 1 below.

PCL has slow degradation rate of ~2 years, it is a very ductile polymer and presents low stiffness (modulus of elasticity ~0.21-0.44 GPa). In order to improve PCL mechanical strength, it was formulated with PLA which is stiffer (modulus of elasticity ~3-4 GPa) and also has a low degradation rate (PLLA ~2 years). PLLA is glassy at body temperature with glass-transition temperature of 60° C., whereas PCL is rubbery (glass-transition temperature −60° C.). The elongation at break and strength of the PCL/PLA mixture are therefore improved in relation to pure PLLA.

Since PLLA has a high melting point of ~173° C. compared with PCL melting point (~60° C.), only a small percentage of PLLA (up to 10%) was used for the PCL/PLLA film mixtures.

Four molecular weights of PCL were used in combination with PLLA of 10,000 kDa as a commonly used molecular weight for devices.

TABLE 1

Various combinations of PLLA and PCL used in devices of the invention.

| PCL | PLLA |
| --- | --- |
| 100 | 0 |
| 99.9 | 0.1 |
| 99 | 1 |
| 95 | 5 |
| 93 | 7 |

Film Forming:

PCL/PLLA films were fabricated as follows: 2 g of PCL/PLLA powder was dissolved in 40 ml of dichloromethane, chloroform or ethyl acetate. In case of ethyl acetate, a warm water bath ~40° C. was used to aid dissolution. The solution was cast into a glass Petri dish (9 cm), covered with a lid and placed in a fume hood at room temperature for allow for slow evaporation. The dried film was collected and vacuum dried for 48 h. The thickness of the resulting films was measured with caliper. Rectangular specimens were cut with a scalpel blade into uniform dimensions. The specimens were washed in DDW and were dehydrated in a series of alcohol solutions (70, 80, 90, 100 v/v). The alcohol dehydrated PCL film specimens were vacuum dried for another 48 h and placed in desiccators until use.

Alternatively, PCL/PLLA composites were compounded together by tween-screw compounder and thin films were produced by compression molding.

Film Characterization:

Visual Observations:

Films were tested for their integrity and were tested manually for brittleness, strength and elasticity. Only samples that showed intact surface, elasticity and sufficient strength (did not break upon movement) were selected for mechanical and thermal analysis.

Mechanical Properties

Mechanical properties were determined by Dynamic mechanical analysis (DMA) at different temperatures and frequencies.

Surface Morphology

The surface morphology of the films was imaged using Scanning Electron Microscopy (SEM).

Thermal Properties

Differential Scanning calorimeter (DSC) was used to monitor changes of phase transitions including glass transition and melting point. DSC was a thermodynamical tool for direct assessment of the heat energy uptake occurs in a sample within a regulated increase or decrease in temperature.

Film Response to RF Fields

Response of PCL/PLLA films containing small iron oxide magnetic nanoparticles (MNP) and gold nanoparticles (GNP) to heat induced by radio frequency (RF) field was studied. The inclusion of metallic nanoparticles into PCL/PLLA polymer films was needed for the development of an electro-magnetically triggered device melting. While the specific heating mechanism was different for MNP and GNP, they both led to similar outcomes—significant local heating triggered by electro-magnetic fields.

In previous studies it was shown that small colloidal GNP could significantly heat the environment when placed at moderate RF fields. The temperature of one nM solution could increase by 50° C. within 30 seconds using 15 kV/m field at 13.6 MHz (with 600 W commercial generator).

Magnetic fluid hyperthermia is a far more common technique. A lot of research was done on cancer treatment with controlled heating of MNP. It was demonstrated that tissues containing MNP were heated up to 10° C. by alternating magnetic fields at different frequencies (100 kHz to 10 MHz) and intensities (1-20 kA/m).

The advantages of MNP were high heating capability (up to 900 W/g) and simpler (and cheaper) equipment. Their main disadvantage was that they tend to aggregate at high temperatures; however, in solution nanoparticles were embedded in the polymer thus aggregation was not a problem. GNP required higher frequencies but were very stable—RF heating to temperatures above 70° C. was demonstrated. Combination of the two types of NP enabled more flexibility with other parameters, such as polymer chemistry.

Films containing different concentration of GNP and/or MNP were tested in various electro-magnetic fields to study their dissolution.

The impact of electro-magnetic fields at these frequencies on the human body was very limited, an observation that was not surprising.

Optimizing GNP/MNP Content in Films:

In order to determine the optimal size, shape and concentration of nanoparticles required to generate holes in the films in response to RF electro-magnetic stimuli, different concentrations of GNP/MNP have been incorporated, at different sizes inside the polymer composite during the compounding process. Segments of GNP containing films were subjected to ~10-100 kV/m electro-magnetic fields, at different RF frequencies for different durations and the level of film dissolution was measured. Special attention was given to the size of the holes and the size of the PCL/PLLA particles generated post melting in blood samples.

Core/Shell PCL/PLA/NP NP:Xylitol Monofilament Extrution:

Further fabricated was an RF-responsive shell:envelope of PCL/PLLA:xylitol fiber using coaxial-extrusion. This PCL/PLLA-GNP fiber was used as a platform for textiling process by knitting or braiding of specific medical devices. The xylitol shell provided strength as well as fast dissolution property upon RF induced coat melting/perforation.

Device Examples

Sampling 1:

A sample device was placed in a 2 ml glass vial with 700 µl water. The temperature of the water was measured using fiber thermometer during the application of the magnetic field. The main advantage of this system was good thermal insulation.

Sampling 2:

A sample device in the form of a circular piece of polymer (~2 cm diameter) was placed in an open chamber and directly measured with a thermal camera (FLIR E50). The main advantage here was the direct measurement.

All samples were measured in both sampling systems. In sampling system 1, three samples of each film (from different areas) were measured in triplicate—total 9 measurements per film. In sampling system 2 each film was measured once, with many measurement points in every image (every pixel contained temperature data).

The data below represents an average of 221 pixels taken from the center of a sample in each movie of a thermal camera, giving an average temperature vs. time in different conditions.

1. Concentration Dependence—Particle Dispersion Using Vortex

All films were composed of ~1 g of PCL with different amounts of magnetic nanoparticles (MNPs) at the 10-1000 mg range (the highest concentration not presented). The dry particle powder was mixed with vortex until visual homogeneity. During the drying process some inhomogeneity was observed.

Figure 4:
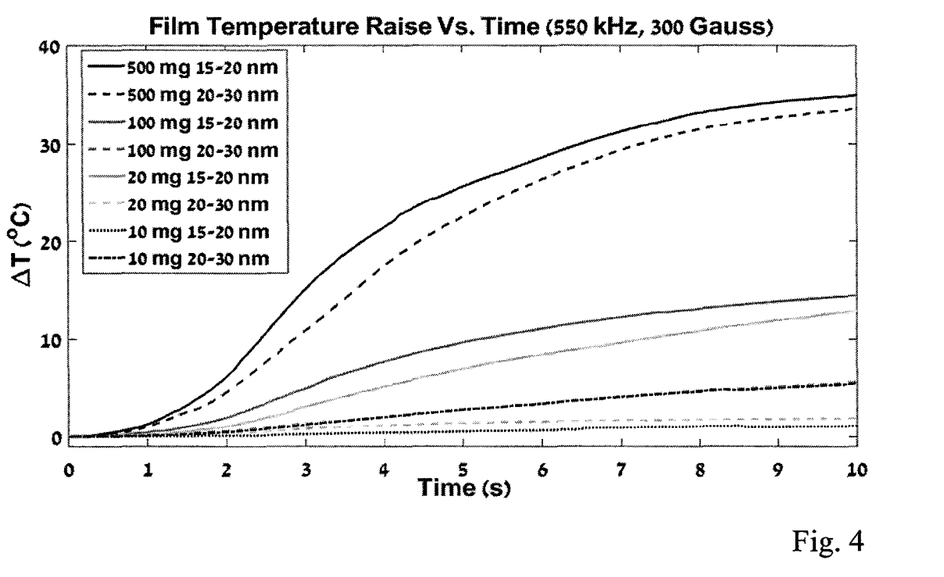
FIG. 4 depicts a change in the temperature of a film comprising different amounts of $Fe_3O_4$, in the first 10 seconds of the application of a field.

The plot presented in FIG. 4 represents the change in temperature in the first 10 seconds of the application of the field for different amounts of $Fe_3O_4$ nanoparticles in the film. Two sizes of MNP were tested—15-20 nm (solid lines) and 20-30 nm (dashed lines).

The temperature of all films increased—from 1.5° C. for the lowest concentration to 35° C. for the highest.

The general trend was clear—increasing the amount of MNPs increased the heating released to the surrounding polymer.

2. Concentration Dependence—Dispersion with Homogenizer

The films were prepared with similar materials and protocols with only a change in the mixing procedure. Instead of vortex, the powder was mixed with the polymer using a homogenizer. The films looked much more homogeneous during the drying process.

Figure 5:
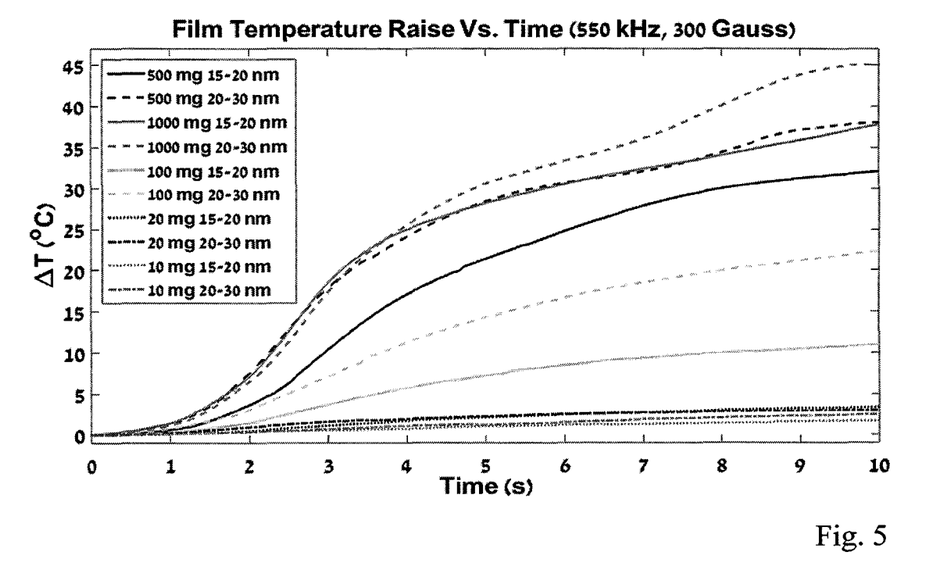
FIG. 5 depicts a change in the temperature of a film prepared with a homogenizer, in the first 10 seconds of the application of a field.

In the plot of FIG. 5 the highest temperature is presented, but it seems that increasing the amount of MNP did not improve the heating, especially not in the first 5 seconds.

The general trend is similar to that observed in FIG. 4, but the anomalies observed in FIG. 4 disappeared. Also, the heating of the most dilute films was slightly improved (2.5° C. vs. 1.5° C.). These two observations may be interpreted as better particle dispersion in the polymer film.

3. Solvents

In these samples the polymer was dissolved in three different solvents before mixing with the MNP—toluene, xylene and dichloroethane. The rest of the preparation protocol was similar to that used for the preparation of the previous films (with homogenizer dispersion).

Figure 6:
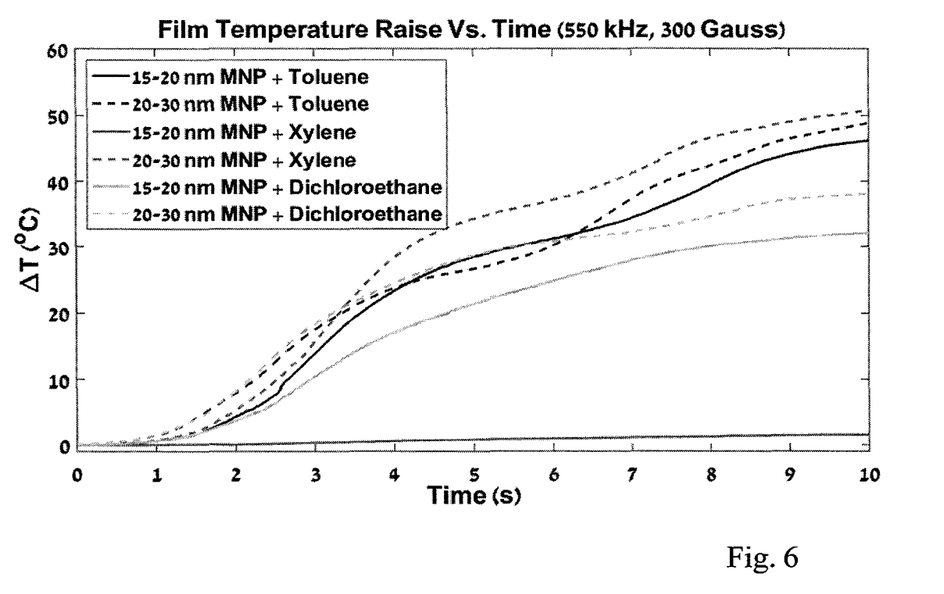
FIG. 6 depicts a change in the temperature of a film in different solvents, in the first 10 seconds of the application of a field.

From the results presented in FIG. 6 it seems that the heating process works similarly with all solvents.

4. Plasticizers 200 mg of TEC and PEG 400 were added to the polymer, the rest of the protocol was identical to above protocol.

Figure 7:
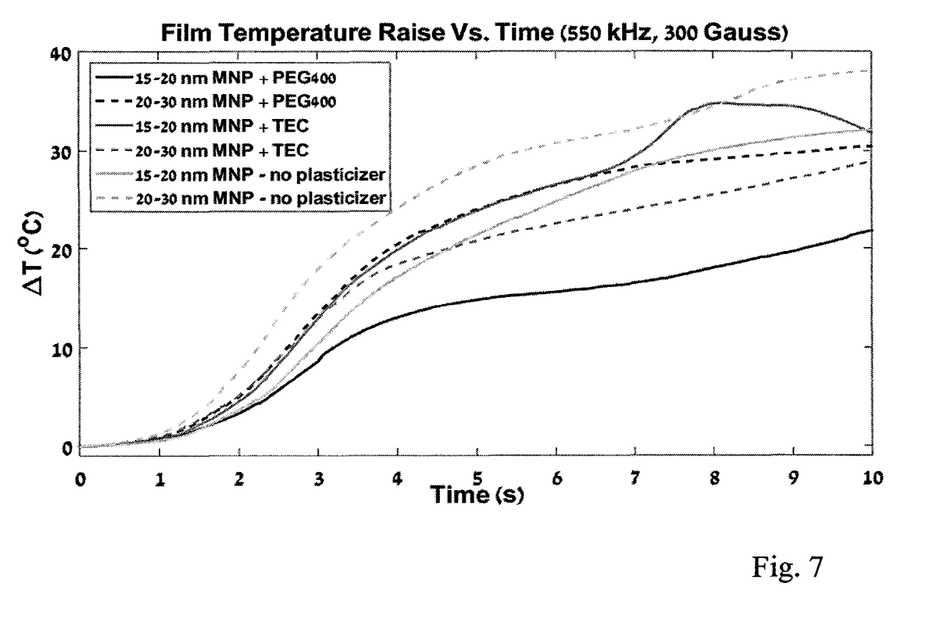
FIG. 7 depicts a change in the temperature of a film comprising different plasticizers, in the first 10 seconds of the application of a field.

From this data (FIG. 7) it seems that the heating capacity was not reduced by the presence of plasticizers. Considering the fact that the sample mass was increased by ~13%, while the temperature difference remained similar or slightly higher, it was possible to speculate that the presence of plasticizers had some (minor) contribution to the heating process. Nevertheless, since the variability in the measurements was higher than 20%, this speculation could not be proven by the results provided in plot.

5. Substrates

Figure 8:
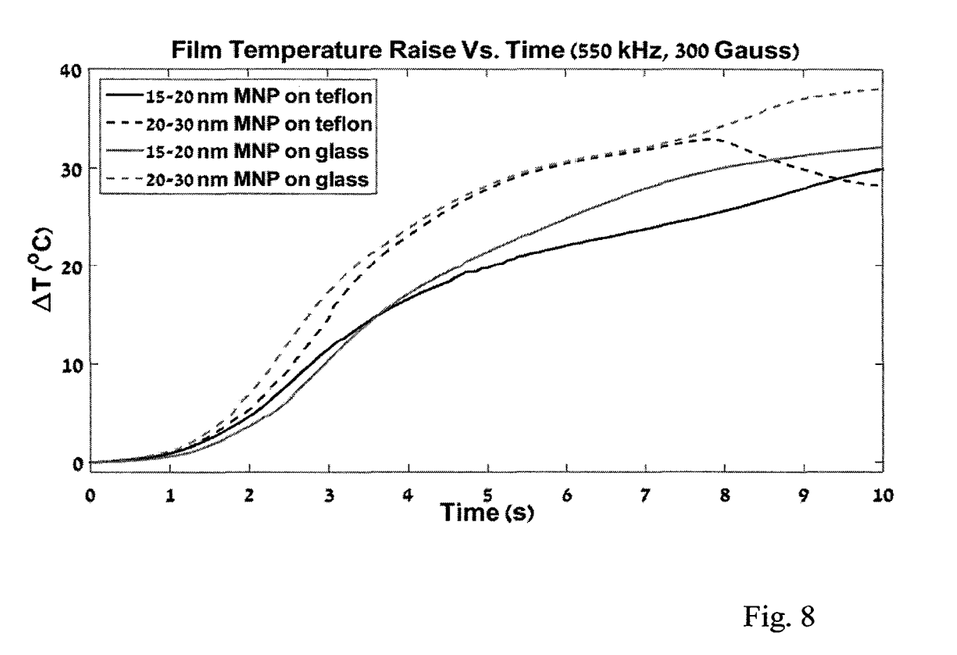
FIG. 8 depicts a change in the temperature of a film formed on different substrates, in the first 10 seconds of the application of a field.

Same films as above were dried onto two different substrates—a flat glass and a Teflon surface. It was expected that the surface would have an effect on the surface roughness and maybe also on the composition of the films. However, the average heating of the polymer was not expected to be affected. Indeed, the four films prepared on different surfaces showed similar behavior (FIG. 8), indicating that the drying surface had no effect on the heating properties. One can speculate that any surface is suitable for film preparation, as long as it is not reacting with the polymer-MNP film.

6. Polymer Length

Four films were examined with different polymer lengths—40 k PCL and 80 k PCL. The rest of the protocol was unchanged.

Figure 9:
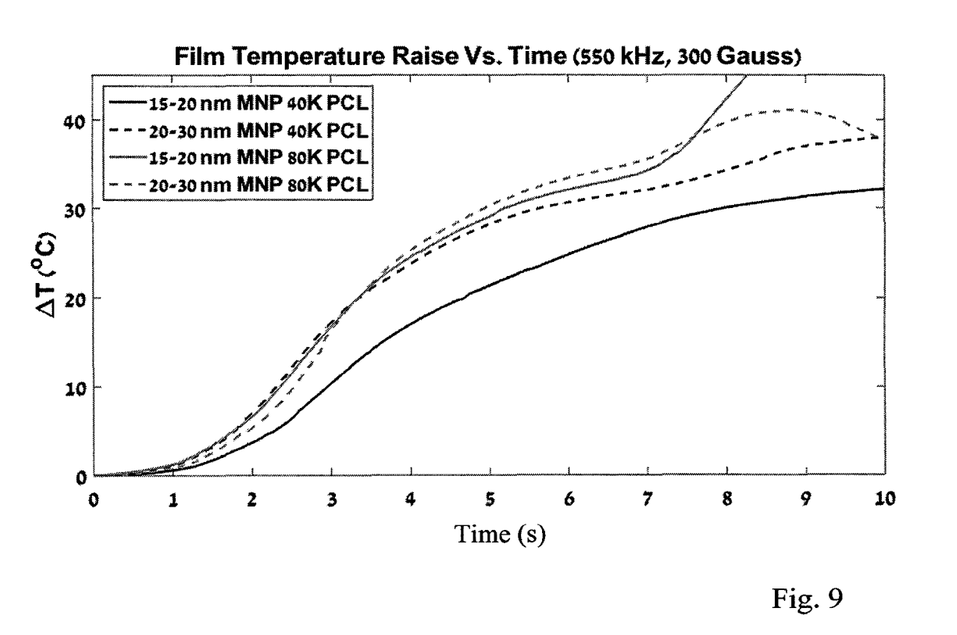
FIG. 9 depicts a change in the temperature of a film formed of polymers of different lengths, in the first 10 seconds of the application of a field.

It seems that the polymer length did not have an effect on the heating properties of the films (FIG. 9).

7. Magnetic Field Magnitude and Frequency

To show that heating is observed even with dilute MNP concentrations, all measurements were done with relatively dilute films—100 mg of 20-30 MNP in 1 g of PCL, dispersed with homogenizer.

Four frequencies were checked with constant magnetic field intensity of 150 gauss: 266 kHz, 308 kHz, 382 kHz and 550 kHz. In all cases there was an increase in temperature of 4-10° C. in 10 seconds.

Field intensity values at the range of 50-300 Gauss were checked with constant frequency of 550 kHz. There was a measurable temperature change in all field intensities, starting at 50 gauss (~0.5° C.), with a significant temperature change (more than 5° C.) above 100 gauss.

The invention claimed is:

1. An implantable medical device comprising:
   a core of at least one biocompatible water-soluble material,
   a skin encasing the core, protecting the core material from water-derived degradation of said core;
   the skin being in the form of a continuous uninterrupted coat around the core, and selected from thermo-degradable (thermo-sensitive) and thermoplastic biocompatible materials, said materials being hydrolytically and physiologically non-degradable and degradable when exposed to an external energy source directed at the device; and wherein the skin optionally comprises at least one radiation responsive material; and wherein the device as a whole is degraded after said skin is exposed to an external energy source directed at the device.

2. The implantable medical device according to claim 1, the device comprising a core of at least one biocompatible water-soluble material, said core being hermetically encased by a skin isolating the material of the core from the environment; the skin being in the form of a continuous uninterrupted coat around the core, and comprising a thermo-sensitive biocompatible material.

3. The implantable medical device according to claim 1, being suitable for implantation within a body cavity or in a subject's tissue, wherein the body cavity or tissue is optionally selected from vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone and joints.

4. The implantable medical device according to claim 1, being in a form selected from a wire, an instrument, prosthetic, implement, contrivance, implant, in-vitro reagent, component, element, accessory or a part which is intended for therapeutic or diagnostic use, in the treatment or prevention or diagnosis of a disease or a condition in a human or an animal.

5. The implantable medical device according to claim 1, wherein thermo-degradable or thermoplastic biocompatible material is selected to be non-degradable in a water-based fluid selected from soft tissue, hard tissue, blood, urine, saliva, sputum, tears, semen, milk, cerebro-spinal fluid and vaginal secretion.

6. The implantable medical device according to claim 1, wherein the core comprises a material selected from natural and synthetic carbohydrates, salts, organic polymers and derivatives thereof.

7. The implantable medical device according to claim 1, wherein the water-soluble material is selected from monosaccharides, di-saccharides, oligosaccharides, polysaccharides and combinations thereof, and active compounds.

8. The implantable medical device according to claim 1, wherein the water-soluble material is selected from glucose, fructose, dextrose, sucrose, manitol, sorbitol, starch derivatives, cellulose derivatives, guar gum, pectins, chitosan, agar, alginate, carrageenans, laminarin sugar alcohols and polyolefins.

9. The implantable medical device according to claim 1, wherein the water-soluble material is selected from xylitol, polyethylene oxide and carbohydrate glass.

10. The implantable medical device according to claim 1, wherein the skin is selected from at least one thermo-degradable or thermoplastic biocompatible material, being hydrolytically non-degradable and physiologically non-degradable and comprising at least one radiation responsive element.

11. The implantable medical device according to claim 1, wherein the thermo-sensitive material maintains a solid form at a temperature below 80° C.

12. The implantable medical device according to claim 1, wherein the thermo-sensitive polymer being selected from poly(acrylamide)s, poly(acrylic acid)s, poly(adipic anhydride)s, poly(7-aminoenanthic acid), poly(12-aminolauric acid), poly(azelaic anhydride), poly(1,3-butadiene-1,4-alt-methacrylonitrile), poly(1,3-butadiene-1,4-alt-methylmethacrylate), poly(butadiene oxide)s, poly(caprolactone), poly(caprylaldehyde), poly(1,4-cyclohexylenedimethylene azelate)s, poly(1,4-cyclohexylenedimethylene dodecanedioate), poly(1,4-cyclohexylenedimethylene glutarate), poly(1,4-cyclohexylenedimethylene) oxymethylene oxide, poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene isophthalate), poly(cyclopropylenedimethylene piperazinediurethane), poly(cyclopropylidenedimethylene oxide), poly (decamethylene), poly(decamethylene carbonate), poly(decamethylene 3,3'-dibenzoate), poly[(decamethylenedioxy)-dihexamethylene oxide], poly(decamethylene disiloxanylenedipropionamide), poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene 3,3'-methylenedibenzamide), poly[decamethylene (methylene-2,5-tetrahydrofuran)-dicarboxamide], poly(decamethylene oxydiacetate), poly(decamethyleneoxymethylene oxide), poly(decamethylene sulfide), poly(decamethylene thiodivalerate), poly(decamethylenethiohexamethylene sulfide), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-caproate], poly[ethylene p-(carboxyphenoxy)-heptanoate] and poly[ethylene p-(carboxyphenoxy)-undecanoate].

13. The implantable medical device according to claim 1, wherein the skin comprises at least one thermo-sensitive material and at least one additive.

14. The implantable medical device according to claim 1, wherein the skin comprises at least one metal or composite inclusions that upon external irradiation heat up and emit heat to their surroundings.

15. The implantable medical device according to claim 10, wherein the at least one radiation responsive element is selected amongst particulate materials.

16. The implantable medical device according to claim 11, wherein the at least one radiation responsive material is distributed in the skin material at different depths.

17. The implantable medical device according to claim 1, wherein the core is of natural or synthetic or semi-synthetic fibers.

18. The implantable medical device according to claim 17, being in the form of a plurality of fibers, each separately provided with a skin of at least one thermosensitive material.

19. The implantable medical device according to claim 18, wherein the fibers are formed into a woven, net-shape, mesh-shape, filter device.

20. A method for non-invasively removing an implantable medical device according to claim 1, the medical device having been implanted in a body of a subject, the method comprising applying a source of thermal radiation at the direction of the device to cause thermal degradation of the device skin and subsequent water-derived degradation of the device core, wherein the thermal radiation is optionally selected from IR, NIR, US, AC induced magnetic or electric field radio frequency (RF), AC magnetic field and AC electric field.

* * * * *